United States Patent
Matsuo et al.

(10) Patent No.: US 11,181,475 B2
(45) Date of Patent: Nov. 23, 2021

(54) GAS ANALYSIS DEVICE

(71) Applicant: Yokogawa Electric Corporation, Tokyo (JP)

(72) Inventors: Junichi Matsuo, Tokyo (JP); Toshiki Miyasaka, Tokyo (JP); Takuya Kawashima, Tokyo (JP); Mamoru Hirono, Tokyo (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 284 days.

(21) Appl. No.: 16/375,668

(22) Filed: Apr. 4, 2019

(65) Prior Publication Data

US 2019/0310188 A1 Oct. 10, 2019

(30) Foreign Application Priority Data

Apr. 6, 2018 (JP) .............................. JP2018-074094

(51) Int. Cl.
*G01N 21/39* (2006.01)
*G01N 21/85* (2006.01)
(Continued)

(52) U.S. Cl.
CPC ......... *G01N 21/39* (2013.01); *G01N 21/3504* (2013.01); *G01N 21/8507* (2013.01);
(Continued)

(58) Field of Classification Search
CPC ... G01N 2201/0224; G01N 2021/8514; G01N 21/39; G01N 1/2247; G01N 2021/392; G01N 2021/399; G01N 21/3504; G01N 21/8507; G01N 2201/0227; G01N 2201/0236; G01N 2201/0245; G01N 33/0009; G01N 2201/06113; G01N 2021/8521; G01N 2021/8578;
(Continued)

(56) References Cited

U.S. PATENT DOCUMENTS 3,041,461 A * 6/1962 Lindemann ............ D03D 51/28
  250/559.43
3,770,355 A * 11/1973 Anthon .................. G01N 21/59
  356/419

(Continued)

FOREIGN PATENT DOCUMENTS

CN 104122416 A 10/2014
CN 104483284 A 4/2015
(Continued)

*Primary Examiner* — Kara E. Geisel
*Assistant Examiner* — Amanda Merlino
(74) *Attorney, Agent, or Firm* — Osha Bergman Watanabe & Burton LLP

(57) ABSTRACT

A gas analysis device includes a light source configured to emit laser beam to a target gas, a reflection body which reflects the laser beam, a light reception device that receives the laser beam reflected by the reflection body, a container which contains the light source and the light reception device, and an alignment mechanism that includes an insertion member inserted from outside of the container to inside of the container to move, along a plane intersecting with the irradiation direction of the laser beam, at least any one of the light source and the light reception device.

19 Claims, 7 Drawing Sheets

(51) Int. Cl.
  *H01S 5/00* (2006.01)
  *G01N 21/3504* (2014.01)
  *G01N 33/00* (2006.01)
  *G01N 1/22* (2006.01)

(52) U.S. Cl.
  CPC ....... *G01N 33/0009* (2013.01); *H01S 5/0071* (2013.01); *G01N 1/2247* (2013.01); *G01N 2021/392* (2013.01); *G01N 2021/399* (2013.01); *G01N 2201/0224* (2013.01); *G01N 2201/0227* (2013.01); *G01N 2201/0236* (2013.01); *G01N 2201/0245* (2013.01)

(58) Field of Classification Search
  CPC ............ G01N 21/31; G01N 2021/3196; H01S 5/0071; G01J 3/42; G02B 27/14
  See application file for complete search history.

(56) References Cited

U.S. PATENT DOCUMENTS

| | | | |
|---|---|---|---|
| 4,408,830 A | | 10/1983 | Wutherich |
| 5,355,083 A | * | 10/1994 | George .................. G01B 7/023 |
| | | | 324/226 |
| 5,751,423 A | | 5/1998 | Traina et al. |
| 6,118,520 A | * | 9/2000 | Harner ............... G01N 21/8507 |
| | | | 356/136 |

FOREIGN PATENT DOCUMENTS

| | | |
|---|---|---|
| JP | S61-203954 A | 9/1986 |
| JP | 2010-185694 A | 8/2010 |

\* cited by examiner

GAS ANALYSIS DEVICE

CROSS REFERENCE TO RELATED APPLICATIONS

The present application claims priority based on Japanese Patent Application No. 2018-074094 filed on Apr. 6, 2018, the contents of which are incorporated herein by reference.

TECHNICAL FIELD

The present disclosure generally relates to a gas analysis device.

BACKGROUND

Japanese Unexamined Patent Application Publication No. 2010-185694 discloses, as a gas analysis device, a gas concentration measurement apparatus that measures the concentration of a target gas in a measurement target gas on the basis of absorption characteristics obtained by irradiating the measurement target gas with a laser beam and scanning the wavelength of the laser beam. This gas concentration measurement device includes a probe inserted into a flow path of a measurement target gas and having a first reflection mirror for reflecting the signal light emitted through the measurement target gas to cause the signal light to make a round trip, a light source capable of irradiating laser beam in a wavelength band absorbed by the target gas in the measurement target gas and scanning its wavelength, an optical path switcher switching an optical path of the laser beam to alternately generate signal light and reference light, an optical detector measuring the strength of the signal light and reference light passed through the measurement target gas, and a calculation unit deriving a concentration of the target gas in the measurement target gas based on a signal light strength and a reference light strength measured by the optical detector.

Incidentally, the gas analysis device as in the above-mentioned related art is required to have an optical system including a light source, a reflection body, and a light reception device be arranged such that, while the gas analysis device is attached to the installation site (e.g., a flue of a boiler and the like), the laser beam emitted from the light source is reflected by the reflection body and enters into the light reception device. However, depending on the installation conditions and situations of the gas analysis device, the light source, the reflection body, and the light reception device may not be necessarily in proper positional arrangement.

For example, since the probe holding the reflection body at the tip has a relatively small diameter (approximately 50 mm) and a length of about 0.5 to 2 m, the probe may deflect by its own weight when the probe is attached in a cantilevered manner to the inside the flue, the position and orientation of the reflection body may deviate from the design value. A container that contains the light source and the light reception device may also slightly deflect by its own weight when the container is attached in a cantilevered manner to the outside of the flue, and the positions and orientations of the light source and the light reception device may deviate from the design values.

Because the reflection body is located inside the flue, it is difficult to adjust its position and orientation. Therefore, the beam alignment (the position and orientation) of the laser beam needs to be done by moving at least one of the light source and the light reception device arranged outside the flue so that the light source, the reflection body, and the light reception device are brought into proper positional arrangement.

Normally, however, the light source and the light reception device are modularized and contained in the container, and it used to be necessary to open the container and directly access the internal module in order to individually adjust the positions of the light source and the light reception device. When the installation site of the gas analysis device is an explosion-proof area like the flue of the boiler, for example, it is not permitted to open the container with the module in an energized state, so realistically it is difficult to perform beam alignment.

SUMMARY

A gas analysis device according to one or more embodiments of the present invention includes a light source configured to emit laser beam to a target gas, a reflection body that reflects the laser beam, a light reception device that receives the laser beam reflected by the reflection body, a container which contains the light source and the light reception device, and an alignment mechanism that includes an insertion member inserted from outside of the container to inside of the container to move, along a plane intersecting with the irradiation direction of the laser beam, at least any one of the light source and the light reception device.

Further features and aspects of the present invention will be understood from the detailed description of the embodiments described below with reference to the accompanying drawings.

DETAILED DESCRIPTION

Embodiments of the present invention will be described. Those skilled in the art can achieve various alternatives to the embodiments using the teachings of the present invention, and the present invention is not limited to the embodiments described herein.

One or more embodiments of the present invention provide a gas analysis device 1 capable of performing beam alignment of laser light without opening a container that accommodates a light source and a light reception device.

Figure 1:
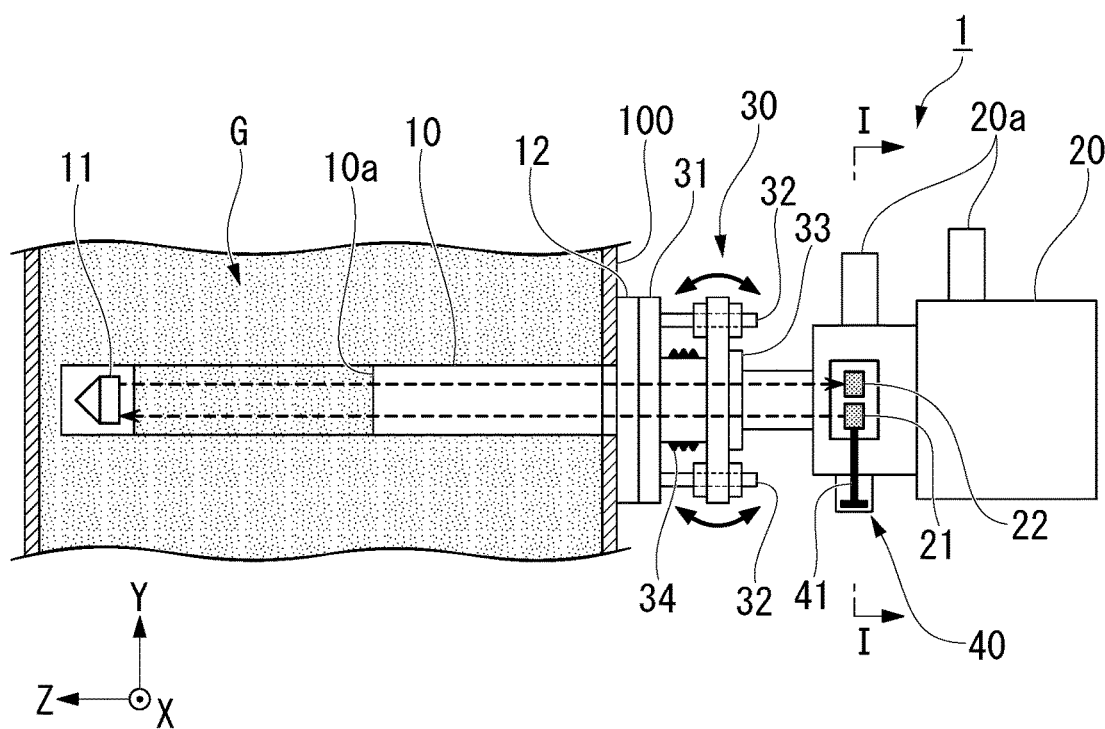
FIG. 1 is a side view illustrating a configuration of a gas analysis device according to one or more embodiments.

FIG. 1 is a side view illustrating a configuration of a gas analysis device 1 according to one or more embodiments.

As shown in FIG. 1, a gas analysis device 1 according to one or more embodiments is installed in a cantilever supported state to a flue 100 of a boiler. The gas analysis device 1 analyzes the concentration of the target component contained in the target gas G (process gas) flowing in the flue 100. The gas analysis device 1 may be, for example, a TDLAS (Tunable Diode Laser Absorption Spectroscopy) type laser gas analyzer.

The gas analysis device 1 has a probe 10 inserted inside the flue 100 and supporting the reflection body 11 and a container 20 arranged outside the flue 100 and containing a light source 21 and a light reception device 22. The probe 10 is constituted by a cylindrical object made of metal and having a circular cross section and its length is about 0.5 to 2 m. In the probe 10, an opening portion 10a is formed, so that the target gas G flowing in the flue 100 can pass through the inside of the probe 10.

On the distal side of the opening 10a of the probe 10, a reflection body 11 is provided. The reflection body 11 is, for example, a corner cube prism or a retro reflector, and causes a laser beam irradiated from the light source 21 to be reflected and reciprocated. This probe 10 is attached via a flange 12 to the outside of flue 100 so that the probe 10 is predominantly located within flue 100.

The container 20 is connected to probe 10 via alignment flange 30 (described below). The container 20 contains a semiconductor laser device as a light source 21, a photodetector as a light reception device 22, a CPU as a calculation unit (not shown), other electronic components, a board on which these are mounted, and the like. The container 20 is an explosion-proof container, and the container 20 is a heavy-weight product. On the outer peripheral surface of this container 20, a backfire prevention device 20a is attached.

The light source 21 emits the laser beam toward the reflection body 11 of the probe 10. The laser beam passes through the inside of the probe 10 and is reflected by the reflection body 11. The reflected laser beam again passes through the inside of the probe 10 and is received by the light reception device 22. When reciprocating inside the probe 10, the laser beam is subjected to light absorption by the target gas G passing through the inside of the probe 10.

The calculation unit finds the concentration of the target component in the target gas G based on the light absorption spectrum of this laser beam. Many gas molecules such as $CO$, $CO_2$, $H_2O$, CnHm (hydrocarbon), $NH_3$, $O_2$, and the like have an optical absorption spectrum due to vibration and rotational energy transitions of molecules in the infrared to near infrared region. Since the light absorption spectrum is unique to the component molecule and absorbance is proportional to the component concentration and the optical path length (Lambert-Beers law), the concentration of the target component can be obtained by measuring the light absorption spectrum strength.

Subsequently, the beam alignment structure of the laser beam of gas analysis device 1 will be explained.

In the following description, the irradiation direction of laser beam is referred to as Z axial direction, the horizontal direction perpendicular to the irradiation direction of the laser beam is referred to as X axial direction, and the vertical direction perpendicular to the irradiation direction of the laser beam is referred to as Y axial direction.

The probe 10 and the container 20 are connected via the alignment flange 30 as described above. The alignment flange 30 adjusts the orientation of the container 20 (i.e., the light source 21 and the light reception device 22). The alignment flange 30 according to one or more embodiments adjusts the inclination of the container 20 around an X axis (e.g., drooping due to its own weight of the container 20) and can also adjust the inclination of the container 20 around a Y axis.

The alignment flange 30 has a first flange 31, a plurality of alignment rods 32, a second flange 33, and a bellows tube 34. The first flange 31 is fixed to the flange 12 of the probe 10. For example, about four alignment rods 32 are connected to the back side (at the side of the container 20) of the first flange 31 at equal circumferential intervals. A screw groove is formed on the outer peripheral surface of the alignment rod 32, and nuts are screwed to sandwich the second flange 33.

The back side of second flange 33 is fixed to container 20. The bellows pipe 34 connects the first flange 31 and the second flange 33 in a tiltable manner According to the alignment flange 30 of this configuration, the inclination of the second flange 33 (container 20) relative to the first flange 31 (probe 10) can be arbitrarily adjusted by individually adjusting the position of the nuts screwed to the plurality of alignment rods 32.

In addition, the gas analysis device 1 includes an alignment mechanism 40 for adjusting the position of the light source 21 and/or the light reception device 22 (light source 21 in one or more embodiments). The alignment mechanism 40 moves the light source 21 with an alignment shaft 41 (insertion member) from the outside of the container 20 to the inside of the container 20 so that the light source 21 moves on the X-Y plane crossing the irradiation direction (Z axial direction) of the laser beam.

Figure 2:
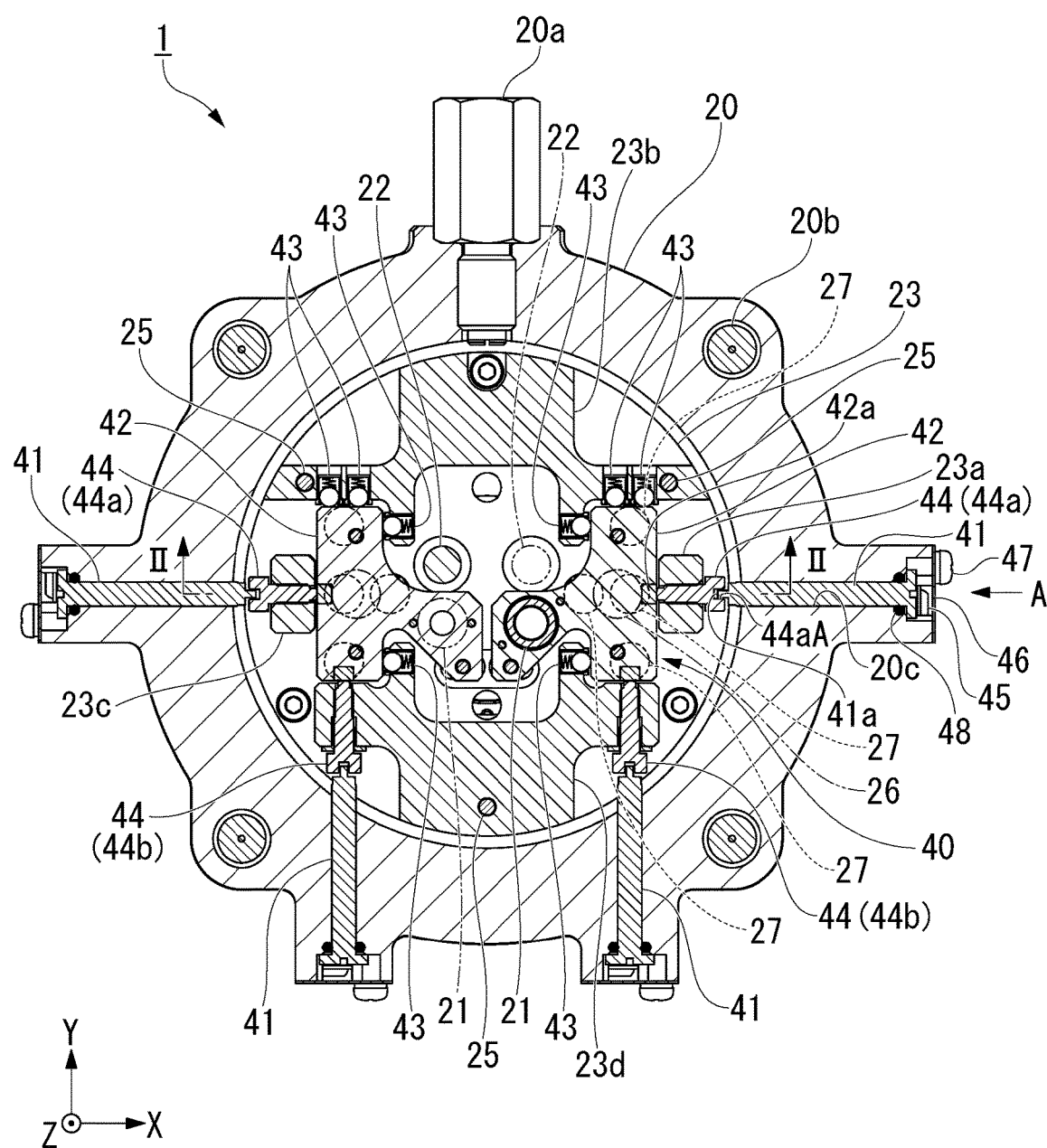
FIG. 2 is a cross-sectional view taken along line I-I illustrating a configuration of an alignment mechanism according to one or more embodiments.
Figure 3:
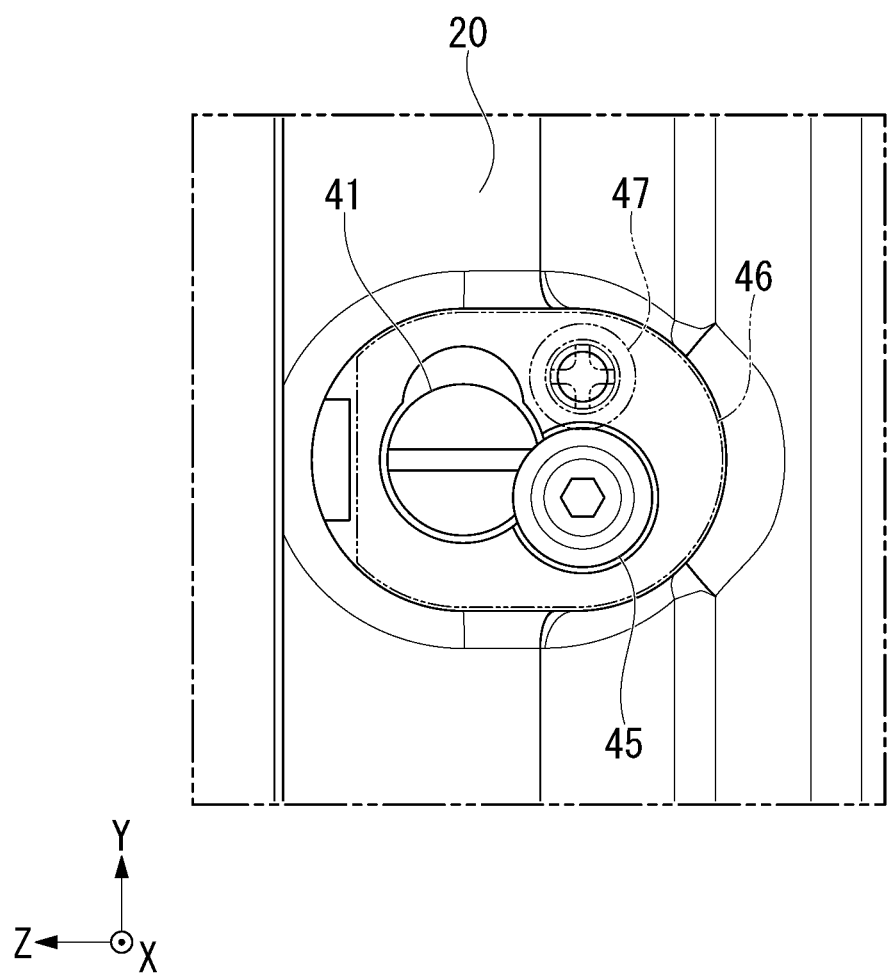
FIG. 3 is a view seen from arrow A illustrated in FIG. 2.
Figure 4:
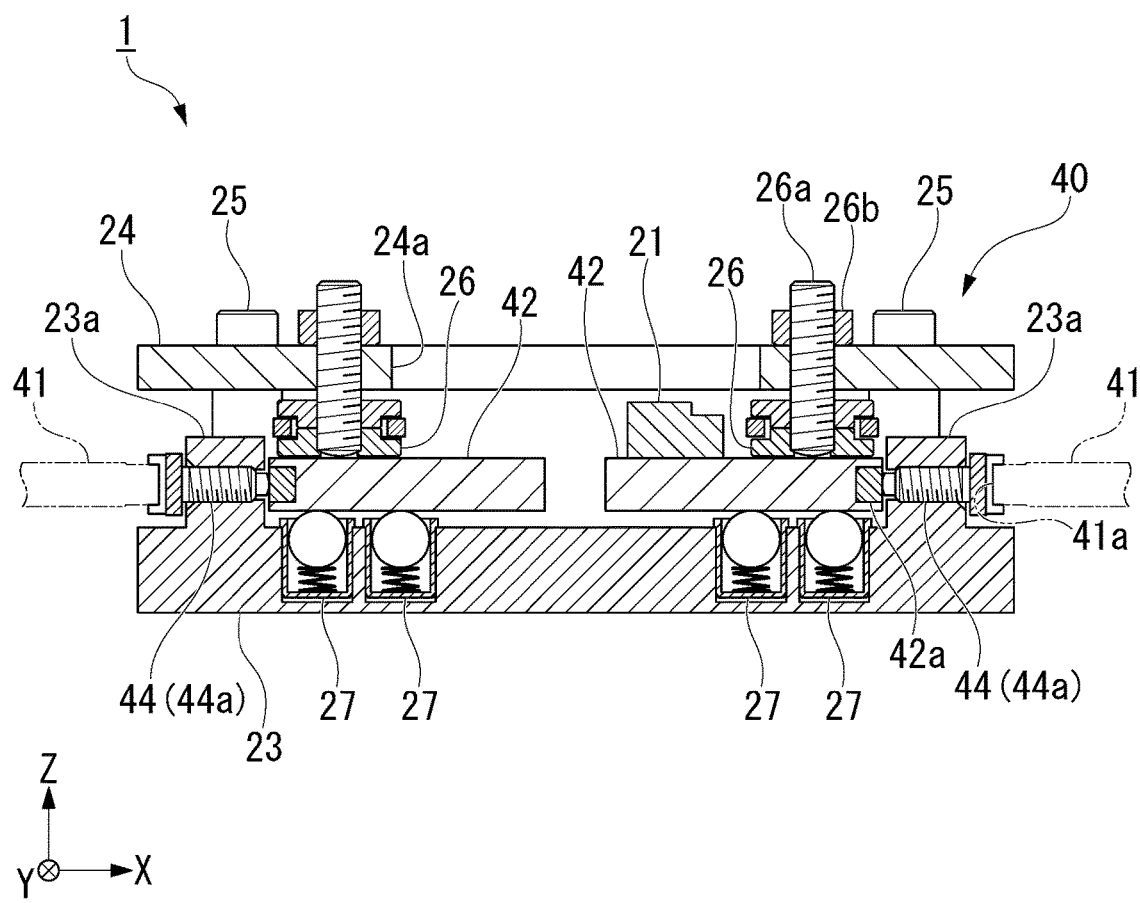
FIG. 4 is a cross-sectional view taken along line II-II illustrated in FIG. 2.

FIG. 2 is a cross-sectional view taken along line I-I illustrating the configuration of the alignment mechanism 40 according to one or more embodiments. FIG. 3 is a view seen from arrow A illustrated in FIG. 2. FIG. 4 is a cross-sectional view taken along line II-II illustrated in FIG. 2.

As illustrated in FIG. 2, a plurality of alignment shafts 41 are passed through the container 20. The container 20 is formed to have a large thickness, and the portion through which the alignment shaft 41 is inserted is formed thicker than the other portions. A fixing bolt 20b for fixing the container 20 to another member (for example, a connection unit with the above-described alignment flange 30) is inserted in the Z axial direction in a thick portion other than the portion through which the alignment shaft 41 is inserted.

The alignment mechanism 40 has a floating base 42 supporting the light source 21. In one or more embodiments, two floating bases 42 are provided in the container 20, and another light source 21 can be attached to the other floating base 42 (the left side in FIG. 2). That is, two pairs of light sources 21 and light reception devices 22 can be set in the container 20. Since the configuration of the two floating bases 42 and the configuration of the peripheral structures are basically similar to each other, the description of the other configuration is simplified or omitted.

The floating base 42 is provided movably along the X-Y plane with respect to a disc-shaped module base 23 mounted inside the container 20. On the module base 23, the light reception device 22 is fixed. The light source 21 and the light reception device 22 have a substantially point symmetric position relationship across the center axis of the module base 23 as viewed from the Z axial direction. In the module base 23, a plurality of protruding units 23a, 23b, 23c, 23d protruding in the Z axial direction are formed.

As illustrated in FIG. 4, a ring plate 24 is attached to protrusion units 23b, 23d opposed to each other in the Y axial direction via a bolt member 25. An opening portion 24a through which the laser beam passes is formed in the ring plate 24. The ring plate 24 supports a slide pad 26 sliding on the floating base 42 on the X-Y plane. The slide pad 26 has a screw axis 26a and a lock nut 26b, and has a configuration capable of making a position adjustable in the Z axial direction.

On the other hand, the module base 23 is provided with a plunger 27 which supports the floating base 42 from the side opposite to the slide pad 26. The plunger 27 has a rotatable ball in contact with the floating base 42 and a spring member for urging the ball toward the floating base 42 in the Z axial direction, so that the plunger 27 supports the floating base 42 to be movably along the X-Y plane and can follow the position adjustment in the Z axial direction of the slide pad 26.

Back to FIG. 2, the push screw members 44 (first push screw members 44a) pushing the floating base 42 in the X axial direction (first axial direction) mesh with protrusion units 23a and 23c opposed to each other in the X axial direction. As the push screw member 44, for example, a fine pitch screw can be used. The tip of the push screw member 44 is in contact with the sliding piece 42a fitted to the side surface of the floating base 42. The plungers 43 (urging mechanism) are arranged on the opposite side of the first push screw member 44a across the floating base 42.

The plunger 43 has a configuration similar the plunger 27 supporting the floating base 42 described above, and has a ball and a spring member, so that the plungers 43 support the floating base 42 movably in Y axial direction, and can follow the position adjustment in the X axial direction of the first push screw member 44a. The plungers 43 are disposed symmetrically with respect to the center line passing through the center of the first push screw member 44a, and a pair of plungers 43 are attached to each of the protrusion units 23b and 23d.

The push screw member 44 (second push screw member 44b) for pushing the floating base 42 is screwed in the Y axial direction (second axial direction) also in the protrusion unit 23d (lower side of the page in FIG. 2). Likewise, the plungers 43 (urging mechanism) are disposed at the side opposite to the push screw member 44b with respect to the floating base 42. The plungers 43 are disposed symmetrically with respect to the center line passing through the center of the second push screw member 44b, and a pair of plungers 43 are attached to the protrusion unit 23b.

The alignment shaft 41 has an engagement unit 41a screwing the push screw member 44. The engagement unit 41a is an example of first engagement unit. The engagement unit 41a has a shape engageable with a slotted groove 44aA provided in the head portion of the push screw member 44. The alignment shaft 41 is inserted into an insertion hole 20c penetrating the container 20 in a radial direction. A small gap (so-called explosion-proof gap) that allows rotation of the alignment shaft 41 and ensures airtightness of container 20 is formed between the outer peripheral surface of the shaft portion of the alignment shaft 41 and the inner wall surface of the insertion hole 20c.

A seal member 48 is disposed on the back side of the head portion of the alignment shaft 41 protruding from the insertion hole 20c to the outside of the container 20. The seal member 48 is an O-ring that seals between the alignment shaft 41 and the insertion hole 20c. The seal member 48 is sandwiched between the alignment shaft 41 and the container 20 to hermetically seal the gap between the alignment shaft 41 and the insertion hole 20c to enhance the airtightness of the container 20.

At the outside of the container 20, a fixing screw member 45 which fixes the alignment shaft 41 in a non-rotatable manner is screwed. As illustrated in FIG. 3, the fixing screw member 45 presses the head portion of the alignment shaft 41 to prevent rotation of the alignment shaft 41 after alignment. Furthermore, outside of the container 20, a lid body 46 is fixed via a screw member 47, and unless the lid body 46 is removed, the alignment shaft 41 and the fixing screw member 45 cannot be accessed.

Subsequently, referring to FIGS. 5A and 5B, operation (action) of the beam alignment structure of gas analysis device 1 having the above configuration will be described.

Figure 5A:
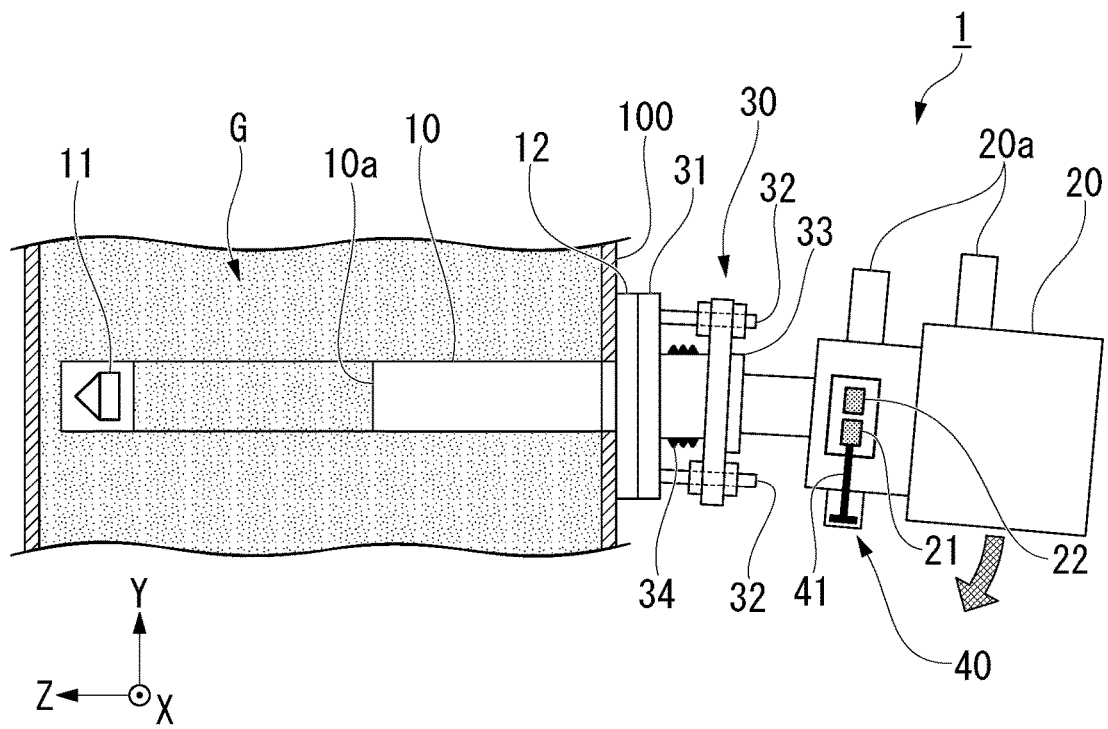
FIG. 5A is a side view illustrating a state of the gas analysis device before beam alignment according to one or more embodiments.
Figure 5B:
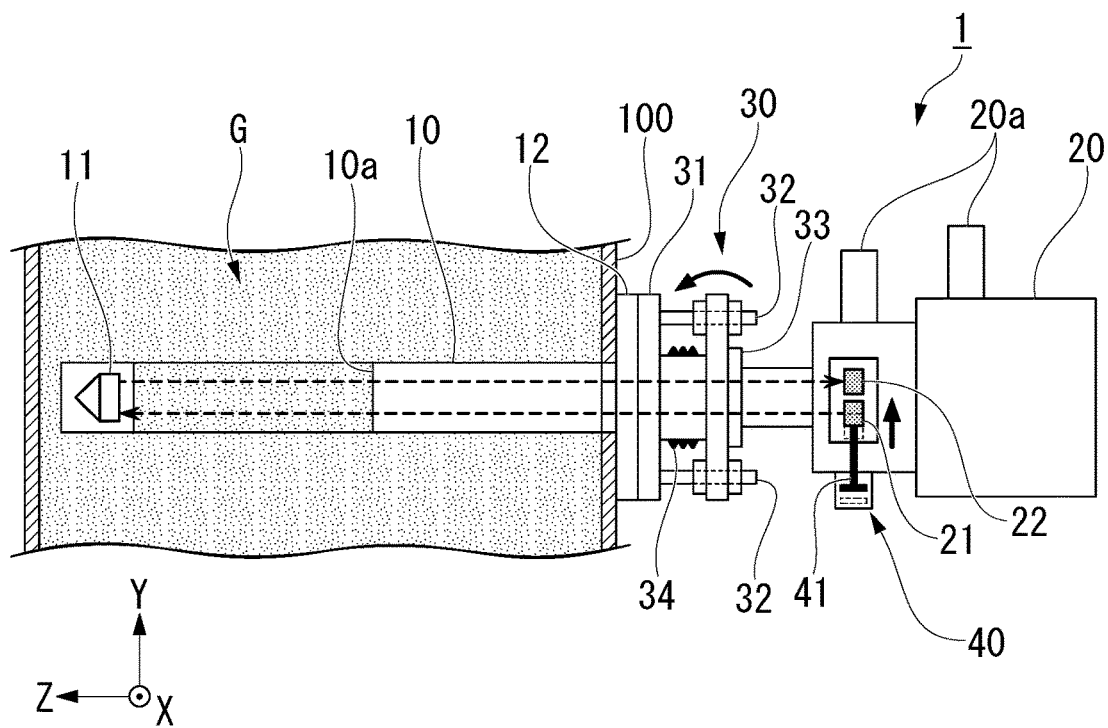
FIG. 5B is a side view illustrating a state of the gas analysis device during beam alignment according to one or more embodiments.

FIG. 5A is a side view illustrating a state of the gas analysis device 1 before beam alignment according to one or more embodiments. FIG. 5B is a side view illustrating a state of the gas analysis device 1 during beam alignment according to one or more embodiments.

As mentioned above, the gas analysis device 1 according to one or more embodiments is mounted in a cantilever supported state to the flue 100 of the boiler. Consequently, the container 20 is an explosion-proof container, and the container 20 is a heavy-weight product, and the deflection due to its own weight is likely to occur as shown in FIG. 5A. When such deflection occurs, there is a concern that the laser beam irradiated from the light source 21 accommodated in the container 20 is deviated from the reflection body 11, or the laser beam reflected by the reflection body 11 does not return to the light reception device 22. Since deflection also occurs at the probe 10, it is desired to perform beam alignment to be described below.

The procedure of beam alignment will be explained. First, as illustrated in FIG. 5B, using the alignment flange 30, the orientation of the container 20 with respect to the probe 10 is adjusted to cause the reflection body 11 and the light reception device 22 to face each other. Next, the alignment shaft 41 is operated from the outside of the container 20 to adjust the position of the light source 21 contained inside the container 20.

The position adjustment of the light source 21 is performed in the energized state while confirming that the laser beam irradiated from the light source 21 is reflected by the reflection body 11 and returned to the light reception device 22 appropriately. After aligning the light source 21 to the appropriate position, the alignment shafts 41 are fixed so that the alignment shafts 41 do not rotate by the adjusting screw member 45 (see FIG. 2).

Thus, the beam alignment of gas analysis device 1 is completed.

As described above, according to one or more embodiments described above, the gas analysis device 1 includes the light source 21 emitting laser beam on the target gas G, the reflection body 11 reflecting the laser beam, the light reception device 22 receiving the laser beam reflected by the reflection body 11, the container 20 housing the light source 21 and the light reception device 22, and the alignment mechanism 40 moving the light source 21 in the X-Y plane crossing the irradiation direction of the laser beam via the alignment shaft 41 inserted from the outside of the container 20 to the inside of the container 20. Since the gas analysis device 1 is configured as described above, the light source 21 can be moved from the outside of the container 20 via the alignment shaft 41 inserted to the inside of the container 20, so that the beam alignment of the laser beam can be performed without opening the container 20.

In one or more embodiments, as shown in FIG. 2, the alignment mechanism 40 is provided movably along the X-Y plane inside the container 20, and the floating base 42 supporting the light source 21 is provided. According to this configuration, the beam alignment of the laser beam can be performed by moving the floating base 42 supporting the light source 21. This eliminates the need for the alignment shaft 41 to directly access the light source 21 and facilitates adjustment of the arrangement of the alignment shaft 41 with respect to the container 20.

In one or more embodiments, the alignment mechanism 40 includes the plunger 43 that urges the floating base 42 along the X-Y plane and the push screw member 44 that pushes the floating base 42 along the X-Y plane against the urging of the plunger 43. The alignment shaft 41 has the engagement unit 41a for screwing the push screw member 44. According to this configuration, the light source 21 can be moved by turning the push screw member 44 via the alignment shaft 41 and pushing the floating base 42. By turning the push screw member 44 in reverse by the alignment shaft 41, the floating base 42 can be pushed back to the original position by the urging of the plunger 43.

In one or more embodiments, the push screw member 44 includes the first push screw member 44a for pushing the floating base 42 in the first axial direction (X axial direction) along the X-Y plane and the second push screw member 44b pushing the floating base 42 in the second axial direction (Y axial direction) along the X-Y plane. According to this configuration, the beam alignment of the laser beam can be performed by translating the floating base 42 in the directions of two axes, i.e., the first axial direction and the second axial direction.

In one or more embodiments, the plungers 43 are disposed symmetrically with respect to the center line passing through the center of the push screw member 44. According to this configuration, the inclination of the floating base 42 pushed by the push screw member 44 can be suppressed by the plungers 43 arranged symmetrically.

In one or more embodiments, the alignment mechanism 40 has the fixing screw member 45 which fixes the alignment shaft 41 to the container 20 so as to prohibit rotation of the alignment shaft 41. According to this configuration, it is possible to fix the alignment shaft 41 to the container 20 so that the alignment shaft 41 cannot be rotated after alignment.

In one or more embodiments, the container 20 has the insertion hole 20c through which the alignment shaft 41 is inserted and has the seal member 48 which seals between the alignment shaft 41 and the insertion hole 20c. According to this configuration, since the gap between the alignment shaft 41 and the insertion hole 20c is sealed, the airtightness of the container 20 through which the alignment shaft 41 is inserted can be maintained.

In one or more embodiments, since the container 20 is an explosion-proof container, the beam alignment of the laser beam can be performed without opening the explosion-proof container in the energized state even with the gas analysis device 1 installed in the explosion-proof area as described above.

Next, additional embodiments of the present invention will be explained. In the following description, the same reference numerals are given to the same or equivalent elements as those in the above embodiments, and the description thereof will be simplified or omitted.

Figure 6:
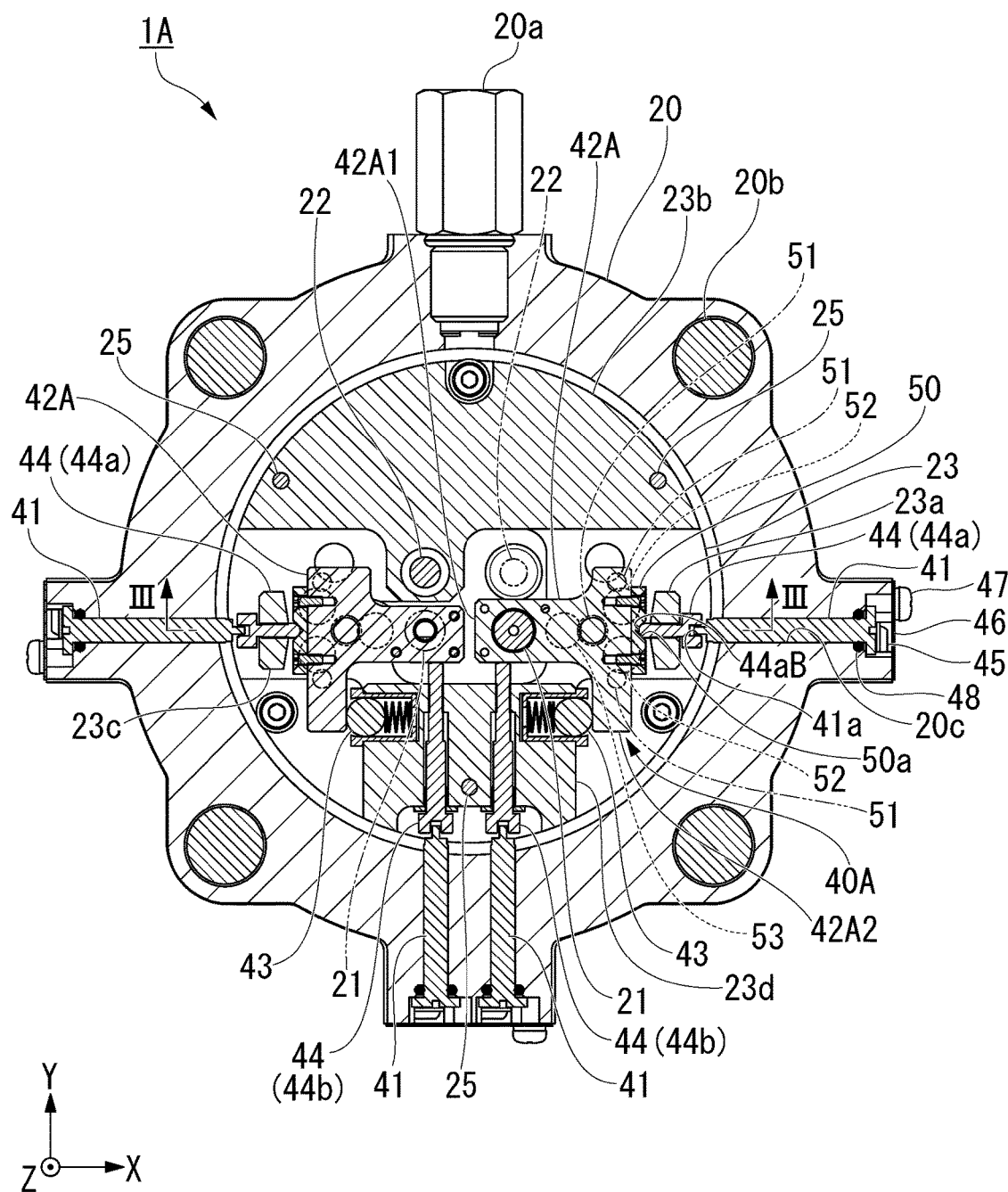
FIG. 6 is a sectional view illustrating a configuration of an alignment mechanism according to one or more embodiments.
Figure 7:
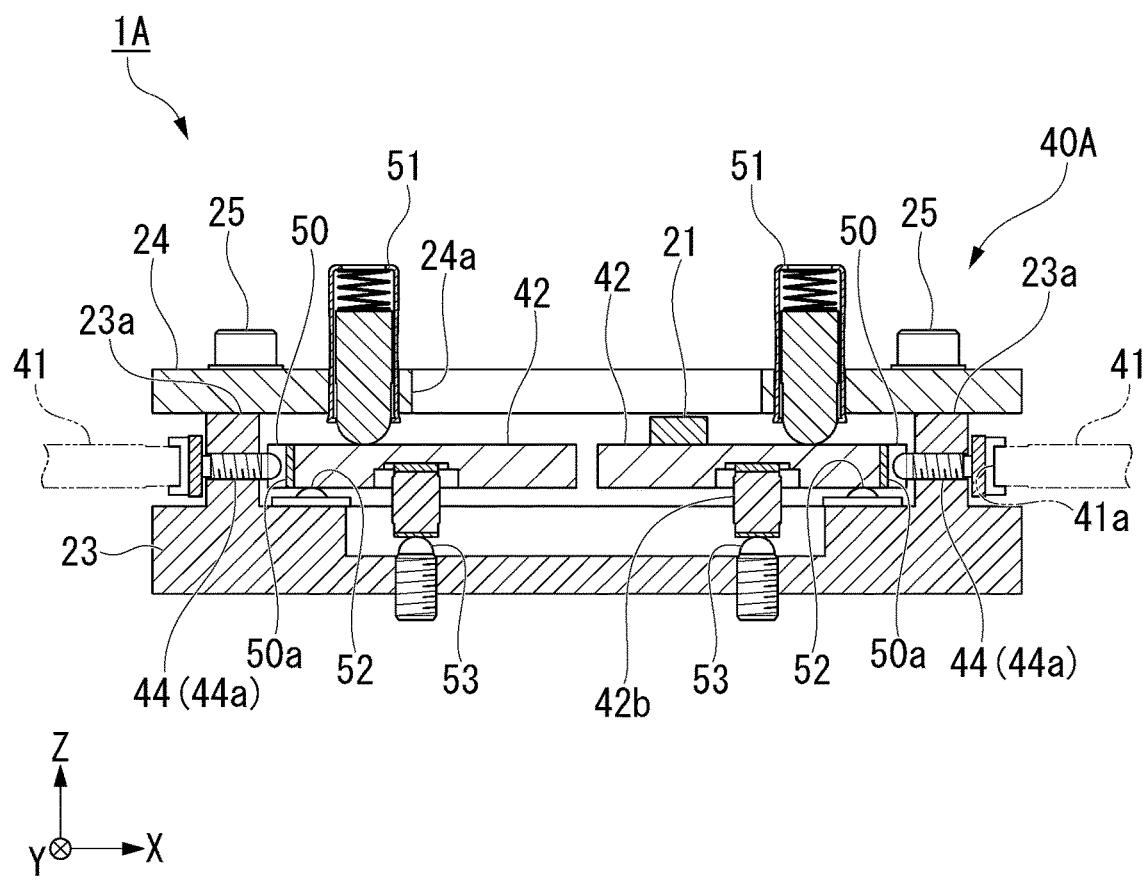
FIG. 7 is a cross-sectional view taken along line illustrated in FIG. 6.

FIG. 6 is a sectional view illustrating a configuration of an alignment mechanism 40A according to one or more embodiments. FIG. 7 is a cross-sectional view taken along line illustrated in FIG. 6.

As illustrated in FIG. 6, the alignment mechanism 40A according to one or more embodiments is different from the previously-described embodiments in that it has an engagement member 50 that converts the movement of the floating base 42A due to the pushing of the second push screw member 44b into swinging motion around a Z axis perpendicular to the X-Y plane.

The engagement member 50 is fixed to the side of the floating base 42A. This engagement member 50 has an engagement groove 50a engaging with the tip 44aB of the first push screw member 44a. The engagement groove 50a has a V-shaped groove. On the other hand, the tip 44aB of the first push screw member 44a is formed into a hemispherical shape. The engagement groove 50a is an example of second engagement unit. The tip 44aB of the first push screw member 44a is an example of third engagement unit.

The floating base 42A according to one or more embodiments is formed in a substantially L shape as viewed from the Z axial direction, and includes a first straight line portion 42A1 extending in the X axial direction from the fixing position of the engagement member 50 and a second straight line portion 42A2 extending in the Y axial direction from the fixing position of the engagement member 50. In the first straight line portion 42A1, the light source 21 is supported. The first straight line portion 42A1 can be pushed in the Y axial direction by the second push screw member 44b.

When the first straight line portion 42A1 is pushed in the Y axial direction by the second push screw member 44b, since the first push screw member 44a is engaged with the engagement member 50, the floating base 42A swings around the Z axis around the tip 44aB of the first push screw member 44a, so that the second straight line portion 42A2 approaches the protrusion unit 23d of the module base 23. In order to achieve this movement, the plunger 43 is attached to the protrusion unit 23d so as to face the second straight line portion 42A2 in the X axial direction.

As illustrated in FIG. 7, the floating base 42A is slidably supported in the X-Y plane by the slide pin 53 fixed to the module base 23. A slide stage 42b for reducing friction with the slide pin 53 is attached to the floating base 42A. In the slide pin 53, a screw groove screwed to the module base 23 is formed, and the slide pin 53 is configured to achieve position adjustment in the Z axial direction.

Further, in the module base 23, a plunger 52 that supports the floating base 42A is provided from the same side as the slide pin 53. On the other hand, the ring plate 24 is provided with a plunger 51 which supports the floating base 42A from the side opposite to the slide pin 53. The plunger 51 is provided with a pin member having a hemispherical tip instead of the above-mentioned ball. These plungers 51 and 52 can follow the position adjustment of the slide pin 53 in the Z axial direction.

According to the gas analysis device 1A of one or more embodiments configured as described above, as illustrated in FIG. 6, the floating base 42A has the engagement member 50 engaging with the tip 44aB of the first push screw member 44a, so that the engagement member 50 can convert the movement of the floating base 42A caused by the pushing of the second push screw member 44b into the swinging motion around the Z axis perpendicular to the X-Y plane. Therefore, according to this configuration, the beam alignment of the laser beam can be performed by the movement of the floating base 42A to the X axial direction and the swing of the floating base 42 around the Z axis. According to this configuration, the number of used plungers 43 can be reduced, the number of parts can be reduced, and the ease of assembly can be improved, as compared with the previously-described embodiments in which the floating base 42 is moved to the directions of two axes arranged to cross each other illustrated in FIG. 2.

Although various embodiments have been described with reference to the drawings, the present invention is not limited to the above embodiments. The shapes and combinations of the respective configuration members illustrated in the above-described embodiments are merely examples, and various modifications can be made based on design requirements or the like within the scope not deviating from the present invention.

For example, in the above embodiments, beam alignment is performed by placing the light source on the floating base, but beam alignment may be performed by placing the light reception device on the floating base. Alternatively, beam alignment (alignment with respect to the reflection body) can be performed by placing a light source and a light reception device on the same floating base or beam alignment can be performed by placing a light source and a light reception device respectively on separate floating bases.

For example, in the above embodiments, the plunger is exemplified as an urging mechanism for urging the floating base along the X-Y plane. However, the urging mechanism may be an elastic body such as a plate spring, a coil spring, rubber, or the like.

For example, if a single floating base is moved by a plurality of push screw members from both sides of the X axial direction and from both sides of the Y axial direction, the urging mechanism may not be provided.

Directional terms such as front, back, above, downward, right, left, vertical, horizontal, below, transverse, row, and column as well as any other similar directional terms refer to directions with respect to a device in question. Accordingly, it is to be understood that these terms be interpreted relative to a device in question.

The term "configured" is used to describe a component, unit, or part of a device includes hardware and/or software that is constructed and/or programmed to carry out the desired function.

It is to be understood that terms that are expressed as "means-plus function" in the claims include any structure that can be utilized to carry out the function of the terms.

A term "unit" is used to describe a component, unit, or part of a piece of hardware and/or software that is constructed and/or programmed to carry out the desired function. Typical examples of the hardware may include, but are not limited to, a device and a circuit.

While various embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. A gas analysis device comprising:
   a light source configured to emit a laser beam to a target gas;
   a reflection body reflecting the laser beam, wherein the reflection body includes a corner cube prism or a retro reflector;
   a light reception device receiving the laser beam reflected by the reflection body, wherein the light reception device includes a photodetector;
   a container containing the light source and the light reception device; and
   an alignment mechanism comprising an insertion member inserted from outside of the container to inside of the container to move, along a plane intersecting with an irradiation direction of the laser beam, at least any one of the light source and the light reception device, wherein
   the alignment mechanism comprises:
      a floating base disposed inside of the container to be movable in the plane and that supports the one of the light source and the light reception device;
      a plunger mechanism that urges the floating base along the plane; and
      a push screw member that pushes the floating base along the plane against urging of the plunger mechanism.

2. The gas analysis device according to claim 1, wherein the insertion member comprises a first engagement unit configured to screw the push screw member.

3. The gas analysis device according to claim 2, wherein the push screw member comprises a groove with which the first engagement unit engages.

4. The gas analysis device according to claim 2, wherein the push screw member comprises:
   a first push screw member configured to push the floating base in a first axial direction along the plane; and
   a second push screw member configured to push the floating base in a second axial direction crossing the first axial direction along the plane.

5. The gas analysis device according to claim 4, wherein the insertion member comprises:
   a first insertion member configured to push the first push screw member in the first axial direction; and
   a second insertion member configured to push the second push screw member in the second axial direction.

6. The gas analysis device according to claim 4, wherein the plunger mechanism comprises:
   a first plunger configured to urge the floating base in the first axial direction toward a direction opposite to a direction in which the first push screw member pushes the floating base; and
   a second plunger configured to urge the floating base in the second axial direction toward a direction opposite to a direction in which the second push screw member pushes the floating base.

7. The gas analysis device according to claim 2, wherein the plunger mechanism is disposed symmetrically with respect to a center line passing through a center of the push screw member.

8. The gas analysis device according to claim 6, wherein the first plunger comprises a pair of first urging members disposed symmetrically with respect to a center line passing through a center of the first push screw member, and
   each of the first urging members includes a rotatable ball in contact with the floating base and a spring member for urging the ball toward the floating base.

9. The gas analysis device according to claim 6, wherein the second plunger comprises a pair of second urging members disposed symmetrically with respect to a center line passing through a center of the second push screw member, and
   each of the second urging members includes a rotatable ball in contact with the floating base and a spring member for urging the ball toward the floating base.

10. The gas analysis device according to claim 4, wherein the alignment mechanism comprises a second engagement unit engaging with a tip of the first push screw member to convert movement of the floating base caused by pushing of the second push screw member into swinging motion around a third axis perpendicular to the plane.

11. The gas analysis device according to claim 4, wherein the first push screw member comprises a third engagement unit formed in a hemispherical shape to be engaged with a second engagement unit,
the second engagement unit has a V-shaped groove with which the third engagement unit is engaged,
when the second push screw member is pushed in, the floating base rotates around a third axis about a position where the second engagement unit and the third engagement unit are engaged.

12. The gas analysis device according to claim 1, wherein the alignment mechanism allows the light source and the light reception device to be moved independently from each other.

13. The gas analysis device according to claim 1, wherein the alignment mechanism allows the light source and the light reception device to be moved together.

14. The gas analysis device according to claim 1, wherein the light source comprises a first light source and a second light source,
the light reception device comprises a first light reception device receiving a laser beam from the first light source and a second light reception device receiving a laser beam from the second light source, and
the alignment mechanism allows any one of the first light source and the first light reception device and any one of the second light source and the second light reception device to be moved independently from each other.

15. The gas analysis device according to claim 1, wherein the alignment mechanism comprises a fixing screw member configured to fix the insertion member in a non-rotatable manner with respect to the container.

16. The gas analysis device according to claim 15, wherein the fixing screw member fixes the insertion member in the non-rotatable manner by pressing a portion of the insertion member.

17. The gas analysis device according to claim 15, further comprising a lid body covering the fixing screw member and the insertion member,
when the lid body is attached, a first insertion member is fixed in the non-rotatable manner by the fixing screw member.

18. The gas analysis device according to claim 1, wherein the container is formed with an insertion hole into which the insertion member is inserted, and
the gas analysis device further comprises a seal member sealing between the insertion member and the insertion hole.

19. The gas analysis device according to claim 1, wherein the container is an explosion-proof container.

* * * * *